United States Patent [19]

Hussey

[11] Patent Number: 4,752,288
[45] Date of Patent: * Jun. 21, 1988

[54] DISPOSABLE ENEMA UNIT

[75] Inventor: Richard P. Hussey, West Boxford, Mass.

[73] Assignee: Aid-Pack, Inc., Gloucester, Mass.

[ * ] Notice: The portion of the term of this patent subsequent to Oct. 28, 2003 has been disclaimed.

[21] Appl. No.: 884,989

[22] Filed: Jul. 14, 1986

Related U.S. Application Data

[60] Division of Ser. No. 678,875, Feb. 4, 1985, Pat. No. 4,619,645, which is a continuation-in-part of Ser. No. 579,183, Feb. 10, 1984, abandoned.

[51] Int. Cl.$^4$ .............................................. A61M 3/00
[52] U.S. Cl. ........................... 604/111; 128/DIG. 18; 206/364; 206/497; 206/807; 215/246; 604/172; 604/200; 604/244; 604/263; 604/265
[58] Field of Search ...................... 206/364, 497, 807; 215/233, 246, 251; 604/111, 172, 194, 200, 244, 263, 265; 128/DIG. 18

[56] References Cited

U.S. PATENT DOCUMENTS

| | | | |
|---|---|---|---|
| 825,116 | 7/1906 | Engels | 206/497 |
| 3,873,018 | 3/1975 | Donnay | 206/497 |
| 4,225,049 | 9/1980 | Inoue | 206/497 |
| 4,248,227 | 2/1981 | Thomas | 604/200 |
| 4,335,756 | 6/1982 | Sharp et al. | 206/364 |
| 4,449,631 | 5/1984 | Levenberg et al. | 206/497 |
| 4,475,903 | 10/1984 | Steenhuisen et al. | 128/DIG. 18 |

FOREIGN PATENT DOCUMENTS 2475895  8/1981  France ................. 604/244

Primary Examiner—L. Dewayne Rutledge
Assistant Examiner—Robert L. McDowell
Attorney, Agent, or Firm—Wolf, Greenfield & Sacks

[57] ABSTRACT

A one-piece sealed disposable enema unit with a lubricated rectal tip is disclosed. The rectal tip of the unit is sealed with a break-off tab. Attached to the tab is a sleeve which covers the exterior of the rectal tip and prevents contamination of the lubricant. Before use, the break-off tab must be twisted off and the tab with the attached sleeve removed. Therefore, the unit is tamper proof and security of the contents is insured.

8 Claims, 4 Drawing Sheets

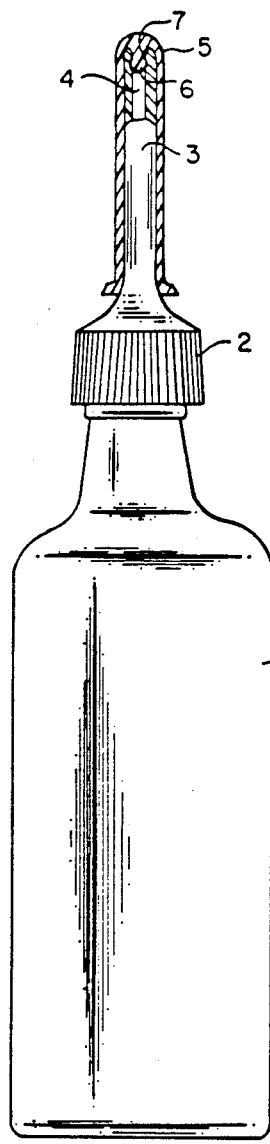
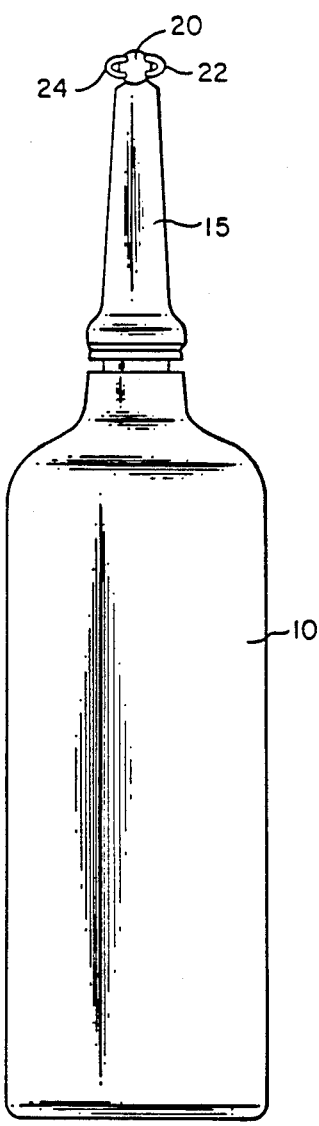
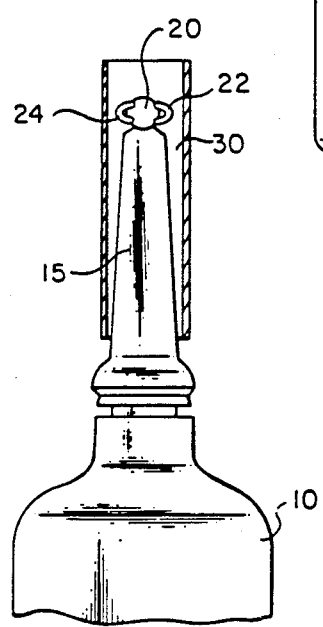
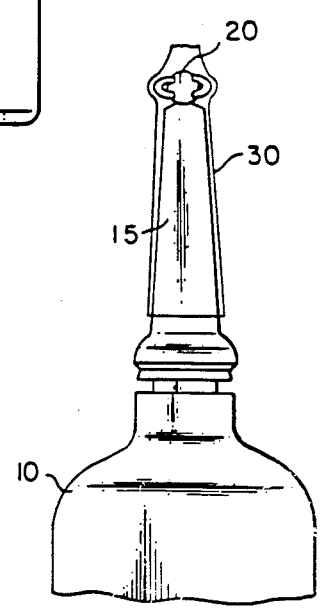
Fig. 1 PRIOR ART
Fig. 2
Fig. 3
Fig. 4

DISPOSABLE ENEMA UNIT

This application is a division of application Ser. No. 06/678,875, filed Feb. 4, 1985, now U.S. Pat. No. 4,619,645, which is a continuation-in-part of application Ser. No. 06/579,183, filed Feb. 10, 1984, now abandoned.

FIELD OF THE INVENTION

This invention relates to medical apparatus and, in particular, to disposable enema units.

BACKGROUND OF THE INVENTION

Conventional disposable enema units consist of a flexible bottle made out of plastic or other material containing an appropriate liquid. The bottle is closed with a screw cap which has an elongated rectal tip that is generally lubricated to ease insertion. Preventing the lubricant on the rectal tip and and the enema fluid from becoming contaminated is of primary importance in the safety and ease of use in such an enema unit.

One prior art approach to maintaining sterility of the enema fluid is to utilize a rubber diaphragm mounted in the screw-on cap. The diaphragm contains a slit which allows the enema fluid to exit from the bottle yet maintains a satisfactory seal to inhibit contaminants from entering the bottle and contaminating the fluid.

Conventionally, the lubricant on the rectal tip is protected by means of a removable sleeve which covers the tip before the unit is used. The sleeve is an elongated tube which is closed at one end. At the closed end, there is mounted a finger which extends inside the sleeve. The end of the rectal tip is constricted and engages the finger to hold the sleeve in place by friction. Before use, the sleeve is pulled off the rectal tip exposing the lubricant.

One problem with the conventional approach for protecting the enema fluid and lubricant is that the unit is not positively sealed so that any pressure on the bottle causes leakage of the enema fluid past the diaphragm slit, in turn, causing contamination and inconvenience. In addition, contraction of the fluid in the bottle due to temperature variations can draw contaminants into the bottle. Further, the tip-protecting sleeve is easily detached and can come loose during shipping or in storage allowing contaminants to reach the tip lubricant.

In addition the prior art unit is not tamper proof because it is possible to remove the sleeve, insert contaminants and then replace the sleeve without leaving any readily visible signs of improper entry. To guard against this problem prior art units are normally sold in a sealed container, an expedient which increases the cost of the units.

It is therefore an object of the present invention to provide an enema unit which is completely sealed to prevent contaminants from reaching the enema fluid.

It is another object of the present invention to provide an enema unit which cannot be opened without physically and visibly breaking the unit so that contaminants cannot be introduced undetectably.

It is yet another object of the present invention to provide a covering for the lubricant on the rectal tip which covering cannot come off in storage or in shipping, yet is easily removed for use.

It is a further object of the present invention to provide an enema unit which is inexpensive and easy to manufacture.

It is still another object of the present invention to provide an enema unit which can be easily opened.

SUMMARY OF THE INVENTION

The foregoing objects are achieved and the foregoing problems are solved in one illustrative embodiment of the invention in which a disposable enema unit comprises a sealed bottle. The rectal tip of the unit is positively sealed by a break-off tab which can be twisted to remove it from the rectal tip and expose the opening.

A protective sleeve is attached to the break-off tab which covers the rectal tip and its lubricant during shipping or storage preventing contamination. The sleeve and the break-off tab are removed by twisting prior to use exposing the lubricant and simultaneously opening the bottle.

A BRIEF DESCRIPTION OF THE DRAWING

FIG. 1 shows a prior art disposable enema unit.

FIG. 2 shows a side view of the illustrative disposable enema unit with its protective sleeve removed.

Figure 5:
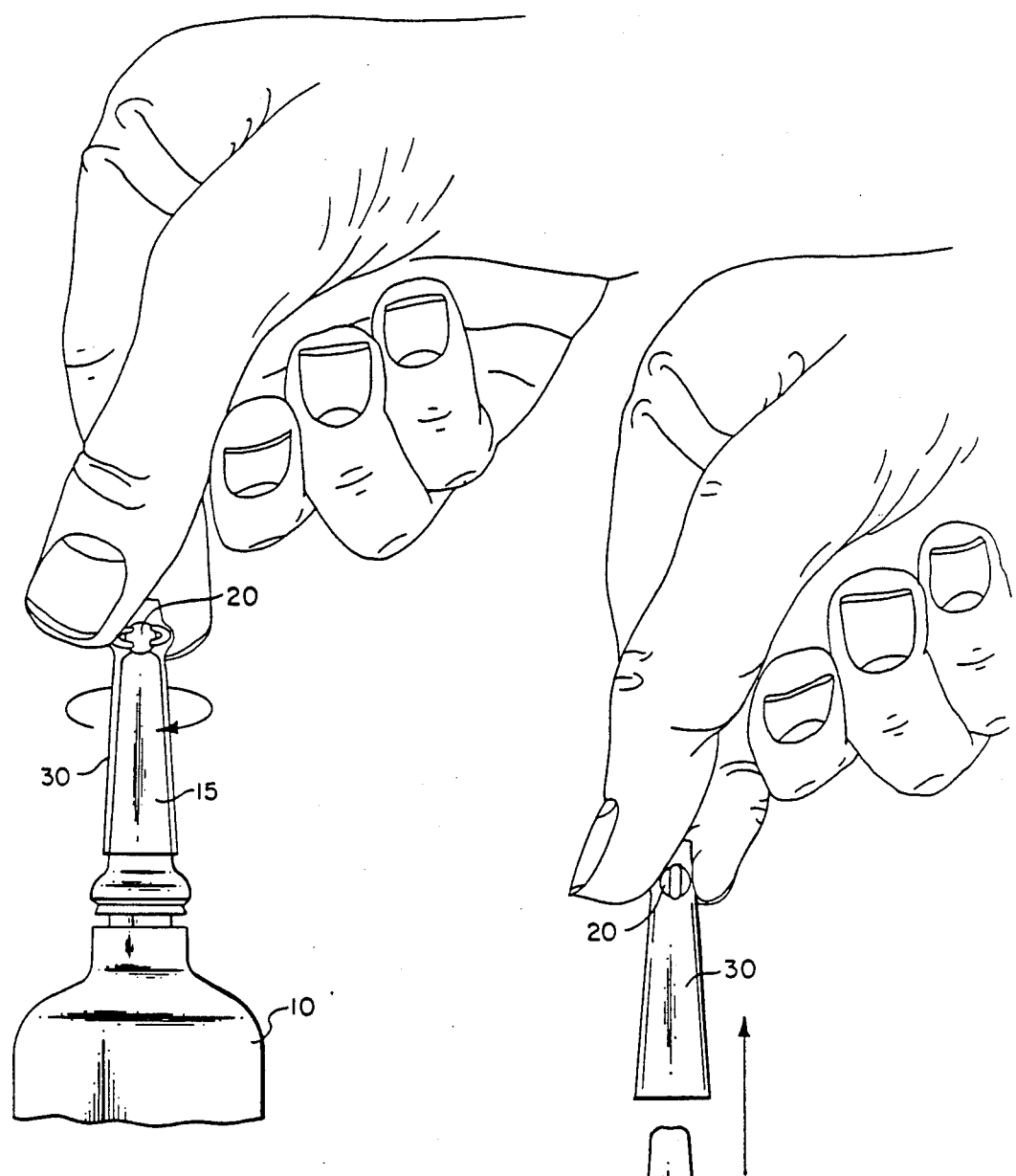

FIG. 3 of the drawing shows a portion of the rectal tip of the inventive enema unit with the protective sleeve in place.

FIG. 4 of the drawing shows a portion of the enema bottle with the protective sleeve shrunk to engage the break off tab.

FIG. 5 of the drawing shows a user twisting the break-off tab to remove it.

Figure 6:
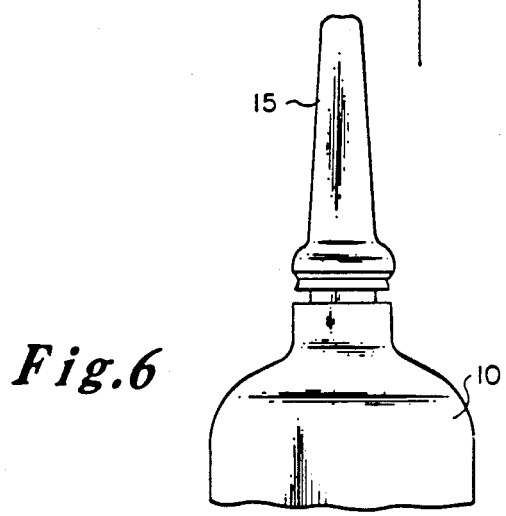

FIG. 6 of the drawing shows the illustrative enema unit with the break-off tab and protective sleeve removed.

Figure 7:
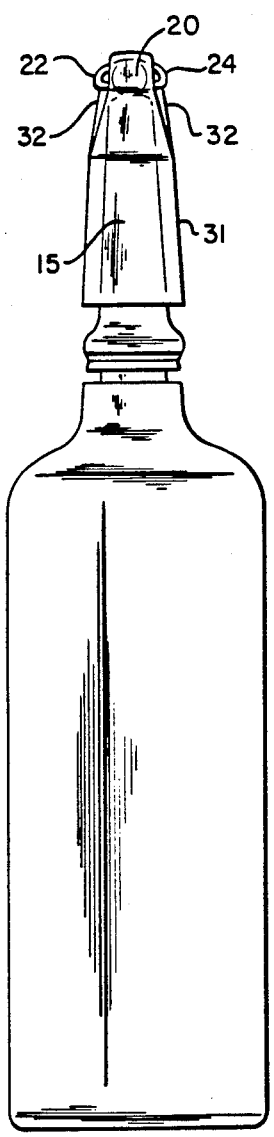

FIG. 7 of the drawing shows a front elevation of the alternate embodiment of the protective sleeve attached to the enama unit.

Figure 8:
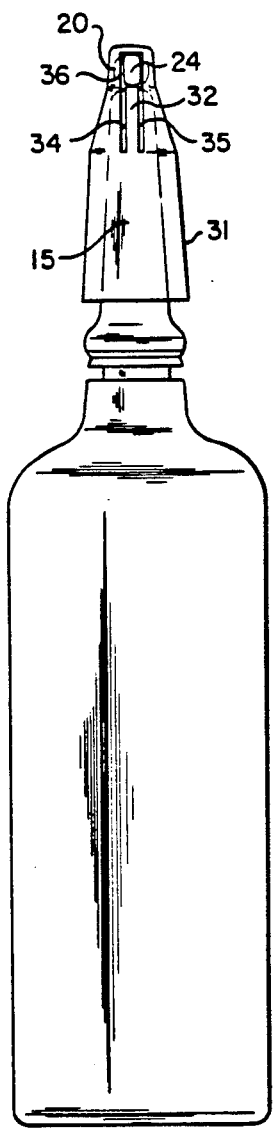

FIG. 8 of the drawing shows a side elevation of the alternate embodiment of the protective sleeve.

Figure 9:
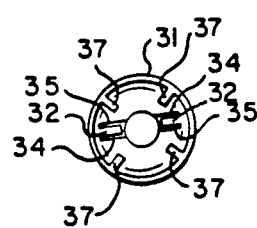

FIG. 9 of the drawing shows a bottom view of the alternate embodiment of the protective sleeve.

Figure 10:
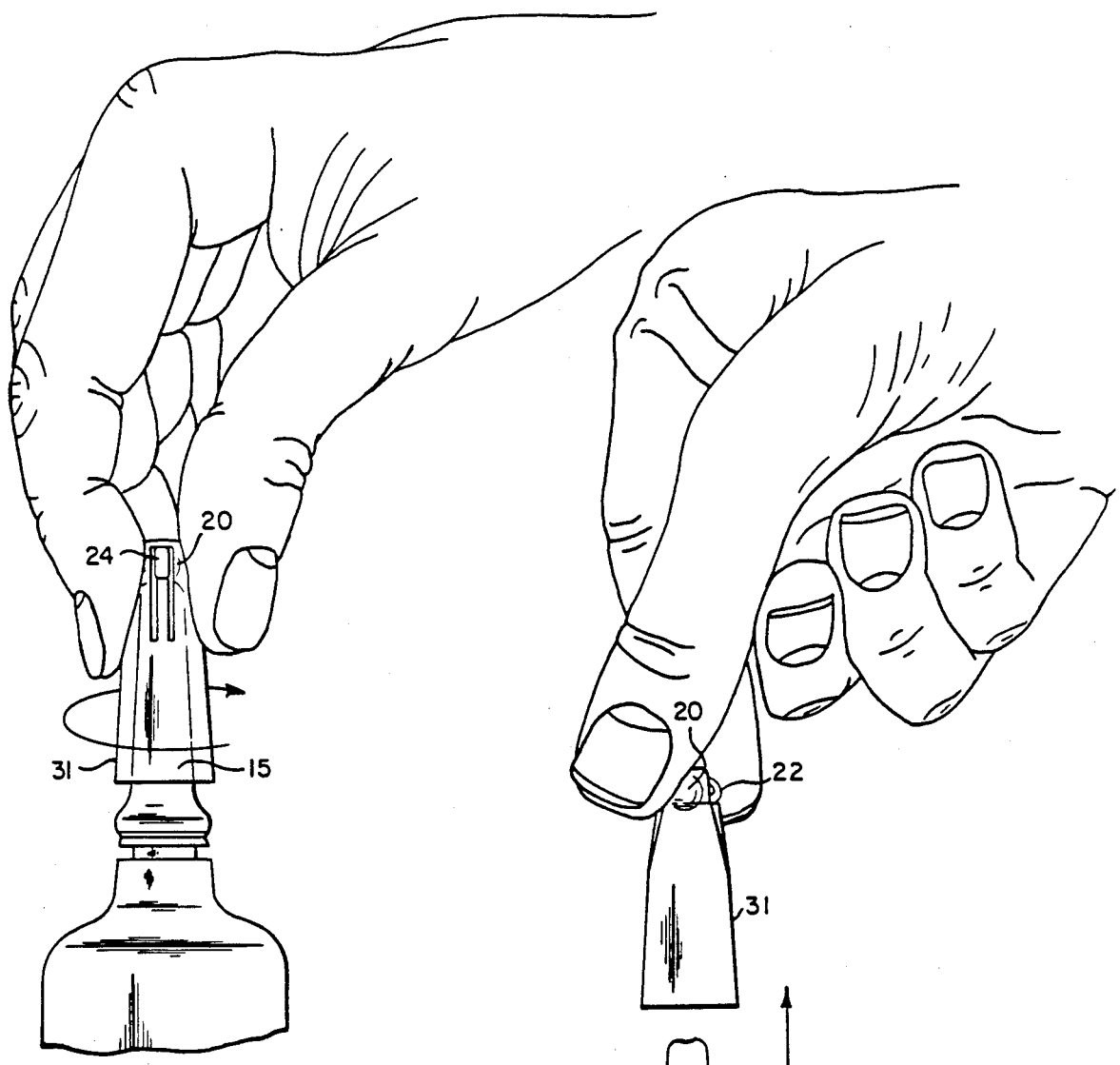

FIG. 10 of the drawing shows a user twisting the alternate embodiment of the sleeve to remove it.

Figure 11:
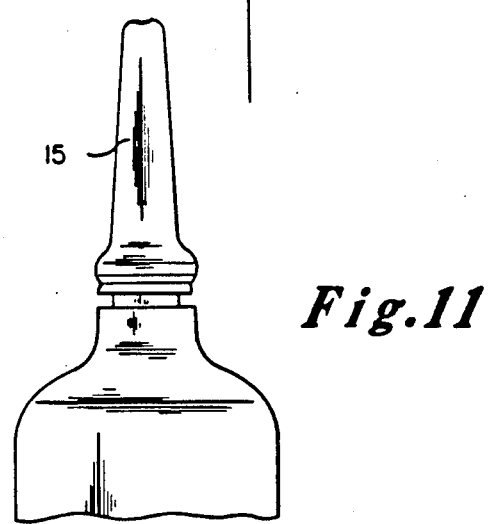

FIG. 11 of the drawing shows the illustrative enema unit with the alternate embodiment of the protective sleeve removed.

DETAILED DESCRIPTION OF THE PREFERRED EMBODIMENT

FIG. 1 of the drawing shows a prior art disposable enema unit consisting of a plastic bottle 1 with a screw cap 2. Screw cap 2 has an elongated rectal tip 3 which is coated with a suitable lubricant. The rectal tip 3 has a cylindrical passage therein to allow passage of the enema fluid. The end of the rectal tip 3 has a constricted ring 7 which engages a finger 6 on protective sleeve 5. Before use, the user removes protective sleeve 5 by pulling upwards causing finger 6 to disengage from ring 7. The disposable enema unit shown in FIG. 1 is typically filled with sterile fluid. Since the engagement between finger 6 and ring 7 must be weak enough to permit easy removal of sleeve 5, as previously described, sleeve 5 often is disengaged during shipping or handling causing spillage of the enema fluid. Cap 2 has a restrictive diaphragm located in the screw on portion. The diaphragm is usually comprised of a resilient material having a slit therein to restrict passage of the enema fluid. When the unit is in use, external pressure on the bottle forces fluid past the diaphragm.

FIG. 2 of the drawing shows the inventive one-piece enema unit. It consists of a bottle portion 10 and a rectal tip 15. Rectal tip 15 and portion 10 may be molded in one piece or may be separate pieces which are joined by suitable and conventional means (such as adhesives) after filling of the enema fluid.

At the top of rectal tip 15 is a break-off tab 20 consisting of a spherical ball 20 which is mounted on the top of rectal tip 15. Ball 20 is of such diameter so that it completely encloses the circular passage through tip 15 (not shown in FIG. 1) preventing spillage of the fluid. Ball 20 may be molded as part of tip 15 with a suitable wall thickness to allow it to be easily removed by twisting. Ball 20 is provided with ears 22 and 24 to allow the ball to be gripped and removed.

During manufacture of the enema unit, tip 15 is coated with a suitable lubricant and a sleeve 30 is slid over the unit as shown in FIG. 3. This sleeve is formed of a heat-shrinkable plastic material which is then heated to the shrinking temperature by conventional means causing it to conform to the ball and rectal tip as shown in FIG. 4. After sleeve 30 has become heat shrunk it is effectively fixed to ball 20 and thereby to the rectal tip 15. Sleeve 30 therefore protects the lubricant against contamination while ball 20 prevents contamination of the sterile enema fluid.

Another embodiment of the protective sleeve which covers the rectal tip is shown in FIGS. 7 and 8. In this embodiment, the protective sleeve comprises a generally barrel-shaped sleeve 31 which tapers toward the top so that the top portion of the sleeve 31 covers only the ball 20 and a small part of the ears 22, 24 where they connect with the ball 20. This arrangement protects the ball 20 from being dislodged by accidental impacts. A pair of diametrically-opposed vertical members 32 formed by lateral slits 34, 35 are located on the sides of the sleeve 31. Above each lateral member 32 is a rectangular opening 36 which is continuous with the lateral slits 34, 35. As the sleeve 31 is pushed over the rectal tip 15, the ears 22, 24 force the lateral members 32 outward and the members 32 snap inward when the ears 22, 24 reach the openings 36, thus preventing removal by pulling but allowing opening of the bottle by twisting. As shown in FIG. 7, the ears 22, 24 protrude through the openings 36 and rest on the members 32 when the sleeve 31 is attached to the unit. As shown in FIG. 9, in this embodiment there are four ribs 37 on the inside of the sleeve 31. The ribs 37 are equally spaced at 90 degree intervals and extend upwardly from the bottom of the sleeve 31 to a location slightly higher than the bottom of the members 32. Ribs 37 separate the sleeve 31 from the rectal tip 15 so that the lubricant thereon is not contaminated. Ribs 37 also orient the sleeve 31 as it is slid onto the unit by guiding the ears 22, 24 to the openings 36. The sleeve in this embodiment is formed separately from the remainder of the enema unit by injection molding and may subsequently be easily attached thereto.

The unit is opened by twisting ball 20 as shown in FIG. 5. This action causes ball 20 to disengage from rectal tip 15, opening the enema fluid passage. Sleeve 30 is then lifted with captured ball 20 and ears 22 and 24 off the unit and discarded and the unit is ready for use, as shown in FIG. 6.

With the preferred configuration it is not possible to easily physically gain access to either the lubricant or the enema fluid without first breaking off ball tab 20. Since this operation physically and visually breaks the package and since the tab cannot be replaced, any improper entry into the package will be readily detectable by examining the integrity of the ball tab. Thus, the package is essentially tamper proof.

Although only one illustrative embodiment of the invention is disclosed herein other modifications which are within the spirit and scope of the invention will be immediately apparent to those skilled in the art. For example, the snape of ball 20 and tabs 22 and 24 may be changed to other configurations without violating the spirit of the invention.

What is claimed is:

1. A container having a tamper-resistant closure comprising:
a molded closed container including an integrally formed section from which at least one break-off tab projects, said tab having means forming an external opening in said container when said tab is moved relative to other portions of said container, and a projective sleeve positioned over and providing a protective environment for said section, said sleeve including means for securing said sleeve to said section and for engaging said tab, whereby on relative movement of said sleeve and tab said sleeve may be removed from engagement with said section and said tab is severed to form said external opening.

2. The container of claim 1, wherein said section is coated with a lubricant.

3. The container of claim 1, wherein said section is elongated and tapered.

4. The container of claim 3, wherein said tab is disposed at the tip of said section.

5. The container of claim 1, wherein said sleeve is comprised of a heat shrinkable material.

6. The container of claim 5, wherein said sleeve is heat shrunk to said tab.

7. The container of claim 1, wherein said sleeve forms an interference fit with said tab.

8. The container of claim 1, wherein said sleeve and tab are adapted to remain engaged when said tab is severed to permit simultaneous removal of said sleeve and tab from said container.

* * * * *